US005285499A

United States Patent [19]

Shannon et al.

[11] Patent Number: 5,285,499

[45] Date of Patent: Feb. 8, 1994

[54] ULTRASONIC FREQUENCY EXPANSION PROCESSOR

[75] Inventors: Dorothy A. Shannon; John P. King, both of Ellicott City; Joseph T. DeWitte, Jr., Laurel; James D. Orndorff, Baltimore, all of Md.

[73] Assignee: Signal Science, Inc., Santa Clara, Calif.

[21] Appl. No.: 52,986

[22] Filed: Apr. 27, 1993

[51] Int. Cl.$^5$ ........................ H04R 25/00; A61B 7/04

[52] U.S. Cl. .................................... 381/68; 381/68.3; 381/67

[58] Field of Search ........................ 381/68, 68.3, 68.2, 381/68.4, 67, 34, 35; 360/8, 32; 395/2

[56] References Cited

U.S. PATENT DOCUMENTS

| | | | |
|---|---|---|---|
| 4,864,620 | 9/1989 | Bialick | 381/34 |
| 4,982,434 | 1/1991 | Lenhardt et al. | 381/683 |
| 5,047,994 | 9/1991 | Lenhardt et al. | 367/116 |
| 5,073,938 | 12/1991 | Galand | 381/34 |
| 5,175,769 | 12/1992 | Hejna, Jr. et al. | 381/34 |

OTHER PUBLICATIONS

Katz, Jack, Handbook of Clinical Audiology, Third Edition, 1985, pp. 108–110.

Portnoff, Michael R., "Time-Scale Modification of Speech, Etc.", IEEE Transactions on Acoustics, Speech, and Signal Processing, vol. ASSP-29, No. 3, pp. 374–390, Jun. 1981.

Lenhardt et al, "Human Ultrasonic Speech Perception", Science, vol. 253, Jul. 1991, pp. 82–85.

*Primary Examiner*—Forester W. Isen
*Assistant Examiner*—Sinh Tran
*Attorney, Agent, or Firm*—Laubscher & Laubscher

[57] ABSTRACT

A method and apparatus for ultrasonic frequency expansion is characterized by expanding audiometric frequencies before translation into the ultrasonic range. The audiometric signals are first expanded in time by a factor of $1/\beta$ where $\beta<1$ while generally maintaining the frequency content of the audiometric signals. Next the frequency of the signals is expanded by a factor $1/\beta$ while compressing the time scale to that of the original signal. The frequency expanded signal is processed via a single-sideband upconverter to translate the frequency expanded signal into a single sideband signal in the ultrasonic range.

6 Claims, 3 Drawing Sheets

ULTRASONIC FREQUENCY EXPANSION PROCESSOR

BACKGROUND OF THE INVENTION

There are noticeable differences in perception of audiometric and ultrasonic signals by human beings. The resolution of human hearing, for example, is measured by a quantity referred to as the Just Noticeable Difference (JND). This parameter is determined experimentally as follows. A subject listens to a tone generated at a certain sound pressure level. The frequency of the tone is then shifted slightly and the JND for that frequency and sound pressure level is the amount of frequency shift which can be perceived by the subject.

Using the JND technique, it has been determined that human hearing operates on a logarithmic scale, so that the resolution at low frequencies is finer, in an absolute sense, than at higher frequencies. Generally, the JND is about 1.4% of the test frequency averaged over different sound pressure levels. For example, a 1 KHz test tone yields a JND of about 14 Hz. The same logarithmic behavior is evident in ultrasonic hearing, but with a larger conversion factor on the order of 12%.

The present invention relates to a method and apparatus for translating audiometric signals into the ultrasonic range. The translated signals can be delivered to an ultrasonic transducer which when properly placed on an individual allows the individual to perceive the ultrasonic signals as audible sound.

BRIEF DESCRIPTION OF THE PRIOR ART

Bone conduction hearing aids are known in the patented prior art as evidenced by the U.S. Pat. Nos. to Lenhardt et al No. 4,982,434 and No. 5,047,994. In these devices, audiometric frequencies are converted to supersonic frequencies in the range of 20 KHz to 108 KHz. The supersonic frequencies are delivered to a transducer mounted on a bony area behind the ear in order to conduct vibrations to the human sensory system. This enables the individual to hear via bone conduction what might otherwise not be heard owing to damage of the individual's auditory nerve or of the individual's air conduction system within the inner ear.

While the prior devices operate satisfactorily, they suffer from certain inherent drawbacks relating to the intelligibility of the signals in the supersonic range.

It is also known in the art to process speech signals for time scaling as disclosed in an article by Michael R. Portnoff entitled Time-Scale Modification of Speech Based on Short-Time Fourier Analysis, IEEE Transactions on Acoustics, Speech, and Signal Processing, Vol. ASSP—29, No. 3, June 1981, p 334–350. With this technique, speech can be speeded up by a factor of three or slowed down by a factor of four while maintaining intelligibility.

The present invention was developed in order to provide a method and apparatus for translating audiometric signals into the ultrasonic range utilizing both time and frequency expansion, whereby the translated signals more accurately represent the original signals for improved hearing via bone conduction, a blood carrying vessel, or by occluding the ear canal.

SUMMARY OF THE INVENTION

Accordingly, it is a primary object of the invention to expand audiometric signals in time by a factor of $1/\beta$ where $\beta<1$ while generally maintaining the frequency content thereof. Next, the frequency of the time expanded signals is expanded by a factor of $1/\beta$ while compressing the time scale to that of the original signal in order to produce a frequency expanded signal. This signal is processed by a single-sideband upconverter to translate the frequency expanded signal into a single sideband signal in the ultrasonic range.

According to another object of the invention, the single sideband signal is amplitude compressed for delivery to an ultrasonic transducer. The transducer is mounted on an individual to deliver the translated signals to the human sensory system.

According to a further object of the invention, the audiometric signal is converted to a digital signal before time expansion and the frequency expanded signal is converted to an analog signal after amplitude compression.

BRIEF DESCRIPTION OF THE FIGURES

Other objects and advantages of the invention will become apparent from a study of the following specification when viewed in the light of the accompanying drawing, in which.

DETAILED DESCRIPTION

Figure 1:
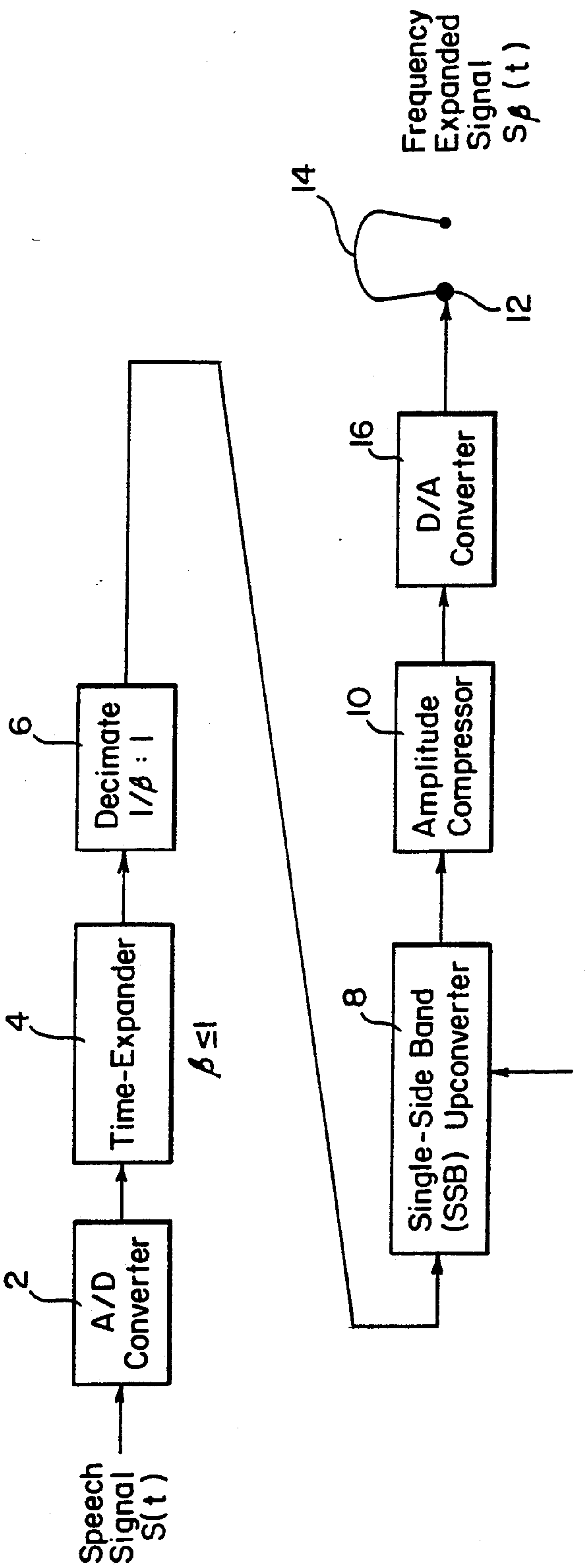
FIG. 1 is a block diagram of the ultrasonic frequency expansion processor according to the invention.

The ultrasonic frequency expansion processor according to the invention will initially be described with reference to FIG. 1. An analog speech signal S(t) in the audiometric range is converted to a digital signal by an A/D converter 2. The digital signal is processed in a time expander 4 to expand the signal in time by a factor or $1/\beta$ where $\beta<1$. During time expansion, the frequency content of the signal is maintained as much as possible. Next, the signal is processed in a decimator 6 to expand the frequency of the time expanded signal by a factor of $1/\beta$ while compressing the time scale to that of the original speech signal.

The time and frequency expanded audiometric signal is next translated to the ultrasonic range. This is accomplished using an analog single-sideband upconverter 8 and an amplitude compressor 10 which compresses the amplitude of the signal in order to achieve better efficiency of an ultrasonic transducer 12 mounted on a headset 14. Compressing the signal after conversion to a single sideband signal results in superior efficiency. Following amplitude compression, the signal is converted back to analog by a D/A converter 16.

The headset is mounted on an individual's head to position the transducer in an optimum position such as on the bony structure behind the individual's ear or near a blood-carrying vessel. The bone or vessel conducts or transmits the ultrasonic signals to the human sensory system enabling the individual to hear the translated audiometric signals. Improved transduction of the signals results from occluding of the ear canal.

Figure 2:
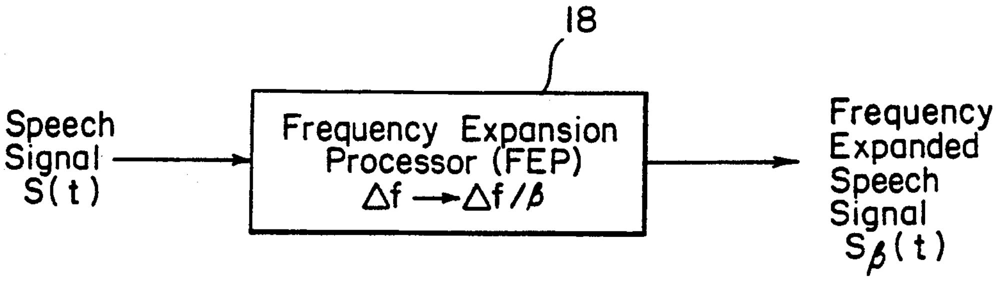
FIG. 2 is a block diagram illustrating the characteristics of the processor of FIG. 1.

Referring now to FIG. 2, the desired properties of the frequency expansion processor (FEP) 18 of FIG. 1 will be described. The processor expands or stretches the frequency f of the audiometric signal by a factor $1/\beta$ while maintaining the same time scale t to produce a frequency expanded speech signal $S_\beta(t)$. An unaltered time scale is important for real time operation. By slowing down the output of the frequency expansion processor, a signal with known characteristics is created, and by analyzing these characteristics, the components of the frequency expansion processor can be determined.

Figure 3:
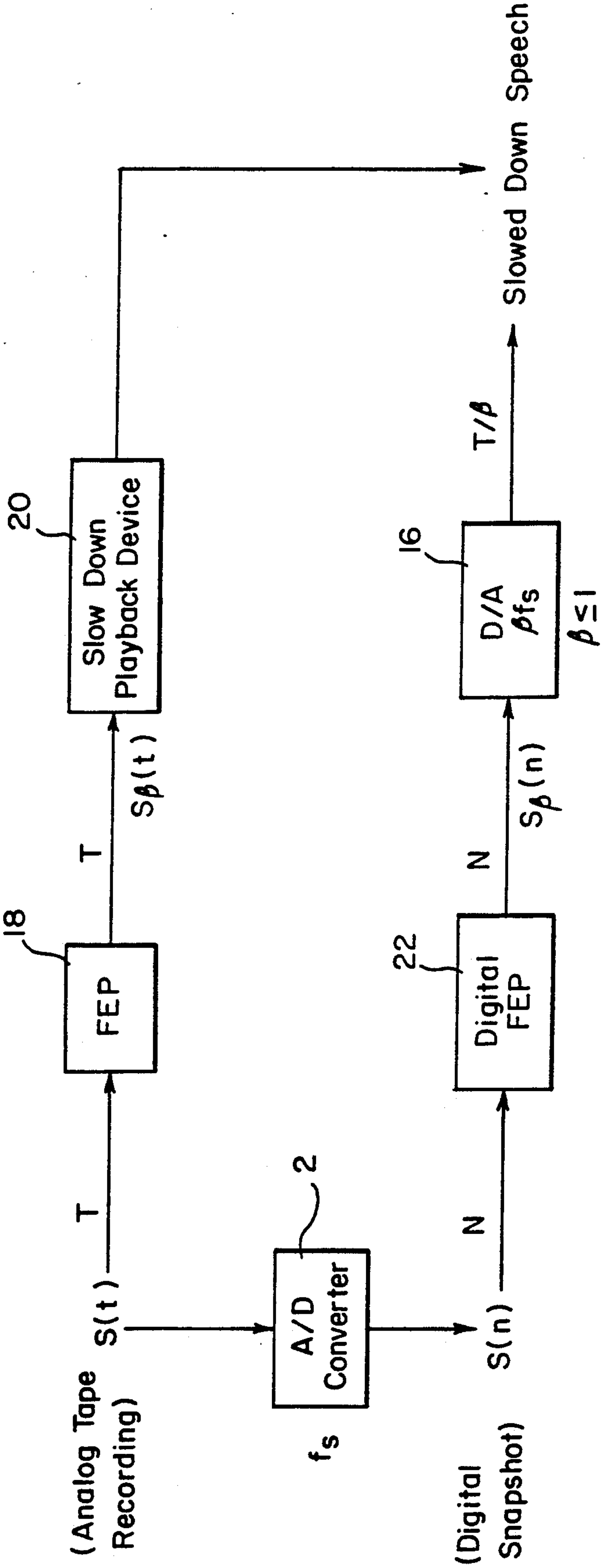
FIG. 3 is a block diagram illustrating the evaluation of the frequency expansion processor.

FIG. 3 shows both analog and digital versions of a batch-mode (non-real time) thought experiment. Slowing down a signal by definition requires batch operation. In the upper (analog) processing sequence, a recorded analog snapshot is played through the FEP 18 which preserves the snapshot duration T but expands the frequencies by a factor $1/\beta$. The output is recorded and the frequency expanded snapshot is played back through a slow down playback device 20 at a speed slower than the original recording speed by a factor of $\beta$. The slowed down playback reverses the frequency expansion of the FEP and expands the time by $1/\beta$. The result is a slowed-down speech signal without pitch shift. The perceived result is that the speech is slower.

Figure 4:
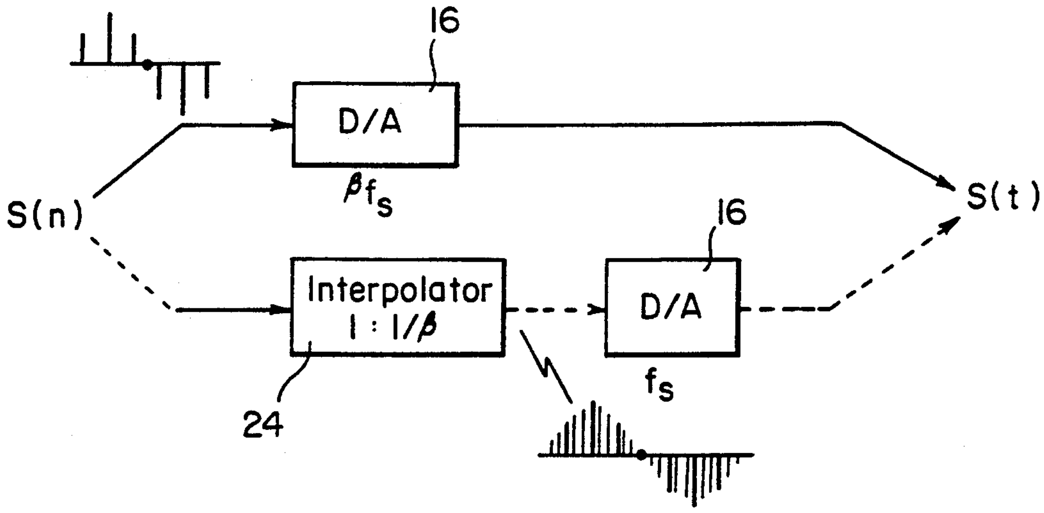
FIG. 4 shows the equivalence of interpolation and slowdown of frequency processing.

In the lower (digital) processing sequence of FIG. 3, the same result is achieved. The speech signal is converted to a digital signal S(n) by the A/D converter 2. After frequency expansion by a digital FEP 22, the signal is converted back to analog by the D/A converter 16. In the digital processing sequence, instead of slowing down the recorded signal, the digital snapshot is played back at a slower rate $\beta f_s$. Alternatively, the sample rate can be maintained at $f_s$ if the D/A converter 16 is preceded by a $1{:}1/\beta$ interpolator 24 as shown in FIG. 4.

One technique for time expansion is described in the aforementioned Portnoff article wherein an algorithm provides time expansion without frequency expansion. An equivalent to the Portnoff technique is to use the FEP followed by a $1{:}1/\beta$ interpolator. Accordingly, the FEP is equivalent to Portnoff's time expander followed by a $1/\beta{:}1$ decimator which is essentially that shown in FIG. 1.

With the method and apparatus of the invention, a high-quality hearing aid for the hearing impaired may be constructed. Sound perception is enhanced through improved formulation of the signal in the ultrasonic range and by expanding the audiometric frequencies before translation into the ultrasonic range. The present invention may provide the only alternative for individuals with severe hearing impairment, especially those individuals suffering certain types of nerve damage. Devices may also be designed for use in high-noise and high-interference environments.

While in accordance with the provisions of the patent statute the preferred forms and embodiments of the invention have been illustrated and described, it will be apparent to those of ordinary skill in the art that various changes and modifications may be made without deviating from the inventive concepts set forth above.

What is claimed is:

1. A method for translating audiometric signals into the ultrasonic range, comprising the steps of (a) expanding the audiometric signals in time by a factor $1/\beta$ where $\beta<1$ while generally maintaining the frequency content thereof;

(b) expanding the frequency of the time expanded signals by a factor $1/\beta$ while compressing the time scale to that of the original signal to produce a frequency expanded signal; and (c) processing said frequency expanded signal via a single-sideband upconverter to translate said frequency expanded signal into a single sideband signal in the ultrasonic range.

2. A method as defined in claim 1, and further comprising the step of amplitude compressing said single sideband signal for delivery to a transducer.

3. A method as defined in claim 2, and further comprising the steps of converting the audiometric signal to a digital signal prior to said time expanding step and converting the frequency expanded signal to an analog signal after said amplitude compressing step.

4. Apparatus for translating audiometric signals into the ultrasonic range, comprising (a) time-expander means for expanding the audiometric signals in time by a factor $1/\beta$ where $\beta<1$ while generally maintaining the frequency content of the signals;

(b) frequency-expander means connected with said time-expander means for expanding the frequency of the time expanded signals by a factor $1/\beta$ while compressing the time scale to that of the original signal to produce a frequency expanded signal; and (c) a single-sideband upconverter connected with said frequency-expander means to translate said frequency expanded signal into a single sideband signal in the ultrasonic range.

5. Apparatus as defined in claim 4, and further comprising a signal compressor connected with said single-sideband upconverter for amplitude compressing said single sideband signal.

6. Apparatus as defined in claim 5, and further comprising an ultrasonic transducer connected with said compressor, whereby when said transducer is mounted on an individual, the translated ultrasonic signals are perceived by the wearer as audible sound corresponding to the audiometric signals.

* * * * *